(12) United States Patent
Campigotto et al.

(10) Patent No.: US 12,245,816 B2
(45) Date of Patent: Mar. 11, 2025

(54) INTRAOCULAR PRESSURE MONITORING CONTACT LENS

(71) Applicants: Queen's University at Kingston, Kingston (CA); Kingston Health Sciences Centre, Kingston (CA)

(72) Inventors: Angelica Campigotto, Kingston (CA); Yong Jun Lai, Kingston (CA); Robert J. Campbell, Kingston (CA); Stephane Leahy, Nepean (CA)

(73) Assignees: Queen's University at Kingston, Kingston (CA); Kingston Health Sciences Centre, Kingston (CA)

( * ) Notice: Subject to any disclaimer, the term of this patent is extended or adjusted under 35 U.S.C. 154(b) by 663 days.

(21) Appl. No.: 17/614,157

(22) PCT Filed: May 29, 2020

(86) PCT No.: PCT/CA2020/050734
§ 371 (c)(1),
(2) Date: Nov. 24, 2021

(87) PCT Pub. No.: WO2020/237385
PCT Pub. Date: Dec. 3, 2020

(65) Prior Publication Data
US 2022/0218202 A1 Jul. 14, 2022

Related U.S. Application Data

(60) Provisional application No. 62/855,132, filed on May 31, 2019.

(51) Int. Cl.
*A61B 3/16* (2006.01)
*A61B 5/00* (2006.01)
(Continued)

(52) U.S. Cl.
CPC .............. *A61B 3/16* (2013.01); *A61B 5/6821* (2013.01); *G02C 7/04* (2013.01); *G16H 50/30* (2018.01); *G02C 2202/06* (2013.01)

(58) Field of Classification Search
CPC .............. A61B 3/14; A61B 3/145; A61B 3/16; A61B 3/165; A61B 5/6821
See application file for complete search history.

(56) References Cited

U.S. PATENT DOCUMENTS

| 10,213,140 B2 | 2/2019 | Pugh et al. |
| 10,772,502 B2 | 9/2020 | Lai et al. |

(Continued)

FOREIGN PATENT DOCUMENTS

| CA | 2961142 A1 | 9/2017 |
| CN | 105919661 A | 9/2016 |

(Continued)

OTHER PUBLICATIONS

Extended European Search Report dated May 15 2023 for corresponding European Patent Application No. 20812566.6.

(Continued)

*Primary Examiner* — David J. McCrosky
(74) *Attorney, Agent, or Firm* — Stephen J. Scribner (57) ABSTRACT

A device for non-invasive monitoring and measuring of intraocular pressure (IOP) of a subject includes a flexible lens that fits on the eye and changes curvature in response to a change in curvature of the eye. A microchannel disposed in or on the lens has one or more ends that are open to the atmosphere and an indicator solution is disposed in a portion of the 5 microchannel. The microchannel exhibits a change in volume in response to a change in curvature of the lens, which results in a change in position of the indicator solution in the microchannel. The change in position of the indicator solution in the microchannel is indicative of a change in IOP.

(Continued)

The change in position of the indicator solution may be detected in digital images of the lens taken with a camera of a mobile electronic device such 0 as a smartphone or a camera worn by the subject.

23 Claims, 8 Drawing Sheets

(51) Int. Cl.
*G02C 7/04* (2006.01)
*G16H 50/30* (2018.01)

(56) References Cited

U.S. PATENT DOCUMENTS

| | | | | |
|---|---|---|---|---|
| 2001/0028309 | A1* | 10/2001 | Torch | A61B 3/113 |
| | | | | 340/576 |
| 2003/0006140 | A1* | 1/2003 | Vacca | G02B 6/3538 |
| | | | | 204/600 |
| 2013/0055819 | A1 | 3/2013 | Yan | |
| 2016/0015265 | A1 | 1/2016 | Mandel et al. | |
| 2016/0262616 | A1* | 9/2016 | Araci | A61B 3/16 |
| 2017/0280997 | A1* | 10/2017 | Lai | A61B 3/16 |
| 2019/0076021 | A1 | 3/2019 | Araci et al. | |
| 2021/0113083 | A1 | 4/2021 | Araci et al. | |

FOREIGN PATENT DOCUMENTS

| | | |
|---|---|---|
| CN | 105962887 A | 9/2016 |
| CN | 109288619 A | 2/2019 |
| EP | 3082570 B1 | 10/2018 |

OTHER PUBLICATIONS

An, H., et al., "Microfluidic contact lenses for continuous non-invasive intraocular pressure monitoring", SPIE Proceedings, vol. 11053, pp. 1105328-1105321 (2019).

An, H. et al., "A method of manufacturing microfluidic contact lenses by using irreversible bonding and thermoforming", Journal of Micromechanics and Microengineer, Institute of Physics Publishing, vol. 28, No. 10, p. 105008, (2018).

* cited by examiner

INTRAOCULAR PRESSURE MONITORING CONTACT LENS

FIELD

This invention relates to non-invasive wearable devices for monitoring and measuring intraocular pressure.

BACKGROUND

Glaucoma is an optic neuropathy in which retinal ganglion cell death occurs leading to progressive vision loss. The disease is the second leading cause of vision blindness in the world. The most important modifiable risk factor for glaucoma is intraocular pressure (IOP); careful monitoring of IOP is a major factor in monitoring the progression of the disease and disease management. IOP levels result from a complex interplay of factors influencing the flow of the aqueous humor within the eye. The aqueous humor brings nutrients to the eye and is central to maintaining eye shape for proper light refraction. In healthy eyes, the aqueous humor drains out of the eye via the trabecular meshwork; however, in individuals with glaucoma there is often increased resistance to outflow and consequently elevated IOP. The IOP has been determined to fluctuate throughout the day based on diet, exercise, water intake, and more; with higher levels found when patients are in the supine position and peak IOP in the early mornings.

Goldmann applanation tonometry (GAT) is the current standard for monitoring the IOP. This procedure uses a device that measures the force required to flatten a specified area of the cornea. GAT requires local anesthesia and a trained eye care professional to perform the test. As a result, patients with glaucoma generally have their IOP measured in a clinic setting, in an upright position, every few months and only within typical office hours. However, IOP levels have been found to vary as much as 10 mmHg or more in a single day. More frequent measuring of IOP is therefore needed.

To address this need various approaches have been proposed, some of which are implanted in the eye and therefore invasive and undesirable. Recently, a continuous monitoring contact lens system, Triggerfish® (Sensimed S A, Lauzanne, Switzerland), has been approved for market. This device is able to continuously monitor the IOP using a contact lens on the patient's eye for up to 24 hours using a flexible adhesive antenna worn around the eye that wirelessly receives a signal from the contact lens, connected via a wire to a dedicated electronic reading and data storage device. Drawbacks of the system are discomfort to the patient who must wear the antenna and carry the electronic device, and significant cost.

Overall, the prior approaches are either invasive or require specialized electronic equipment to obtain the measurement data, which reduce the patient's comfort, and increase the complexity and cost of clinical implementation.

SUMMARY

One aspect of the invention relates to a device for monitoring intraocular pressure (IOP) of an eye of a subject, comprising: a flexible lens that is adapted to fit on the eye and to change curvature in response to a change in curvature of the eye; a microchannel disposed in or on the lens, the microchannel having one or more ends, wherein at least one end is open to a surrounding environment of the lens; an indicator solution disposed in a portion of the microchannel; wherein the microchannel exhibits a change in volume in response to a change in curvature of the lens; wherein the change in volume of the microchannel results in a change in position of the indicator solution in the microchannel; wherein the change in position of the indicator solution in the microchannel is indicative of a change in IOP.

In one embodiment, the microchannel has first and second ends, wherein the first end and the second end are open to a surrounding environment of the lens.

In one embodiment, at least one reference marker disposed on the lens; wherein the change in position of the indicator solution in the microchannel is determined relative to the at least one reference marker.

In one embodiment, the at least one reference marker and the indicator solution are visible in digital images of the device.

Embodiments may comprise a mesh, porous plug, or valve disposed in the at least one open end of the microchannel.

In various embodiments, the microchannel is configured in a convoluted, zig-zag, coiled, spiral, and/or branched shape along a substantial portion of its length. In one embodiment the microchannel comprises a first section configured linearly or in a smooth arc and a second section configured in a convoluted, zig-zag, coiled, spiral, and/or branched shape along a substantial portion of its length. In one embodiment the indicator solution is disposed in the first section of the microchannel.

The microchannel may be configured to occupy a substantial portion of a surface area of the lens. The microchannel may be configured to occupy an outer region of the lens.

In various embodiments, the indicator solution comprises oil or a water-based solution with a naturally-occurring or added pigment, colour additive, or dye.

Another aspect of the invention relates to a method for measuring and/or monitoring intraocular pressure (IOP) of an eye of a subject, comprising: fitting a flexible lens on the eye, the flexible lens being adapted to change curvature in response to a change in curvature of the eye; wherein the flexible lens comprises a microchannel, the microchannel having at least one end that is open to a surrounding environment of the lens, wherein the microchannel exhibits a change in volume in response to a change in curvature of the lens, and an indicator solution disposed in a portion of the microchannel; detecting a change in position of the indicator solution in the microchannel; and correlating the change in position of the indicator solution with a change in IOP.

In one embodiment, the method comprises capturing two or more digital images of the lens at two or more instants in time, respectively; and detecting the change in position of the indicator solution in the microchannel as a difference between the two or more digital images.

In one embodiment, the change in position of the indicator solution in the microchannel is determined relative to a reference marker on the lens.

In one embodiment, the digital images are captured using a digital camera of a personal computing device. The personal computing device may be a smartphone.

In one embodiment, the digital images are captured using a digital camera adapted to be worn by the subject.

Another aspect of the invention relates to system for measuring and/or monitoring intraocular pressure (IOP) of an eye of a subject, comprising: device for monitoring intraocular pressure as described herein; and at least one camera; wherein the at least one camera is adapted to be worn by the subject and to acquire digital images of the device fitted to the eye of the subject.

In one embodiment, the at least one camera is implemented in a frame that is adapted to be worn by the subject.

In one embodiment, the frame is an eyeglasses frame.

In one embodiment, the system includes a software application that is adapted to control the acquiring of digital images by the at least one camera.

BRIEF DESCRIPTION OF THE DRAWINGS

For a greater understanding of the invention, and to show more clearly how it may be carried into effect, embodiments will be described, by way of example, with reference to the accompanying drawings, wherein.

DETAILED DESCRIPTION OF EMBODIMENTS

Embodiments described herein address the drawbacks of prior IOP measuring approaches by providing non-invasive and low cost devices that are easily and conveniently interfaced with readily available equipment. Furthermore, the embodiments also address the need to obtain IOP data more frequently, and outside of regular clinic hours. For the embodiments described, measurement data is obtained optically and may be easily acquired using a camera. For example, readily available cameras such as those found on smartphones and tablet computers may be used for data acquisition. By acquiring images over a period of time, a patient's IOP profile may be precisely determined over time.

Since the shape of the eye, i.e., the corneal curvature, changes in response to changes in IOP, contact lens- (or cosmetic lens-) based embodiments were developed that respond to changes in corneal curvature by deforming, in which an amount of deformation can be directly related to a change in IOP. In general, embodiments are based on a flexible contact lens or cosmetic lens, in and/or on which is disposed a microchannel.

As used herein, the terms "contact lens", "cosmetic lens", and "lens" are used interchangeably and are intended to refer to any type of flexible lens that may be fitted to and worn on the eye, such as, for example, a contact lens or a cosmetic lens. A flexible lens may fit substantially only on the cornea, or it may fit on the cornea and extend outwardly from the cornea to also fit over a portion of the conjunctiva and sclera.

According to the embodiments, at least a portion of the microchannel exhibits a change in volume in response to deformation of the contact lens resulting from a change in corneal curvature. The microchannel has one or more end that is open to the surrounding environment or medium, e.g., the atmosphere (i.e., air). The one or more open end of the microchannel may be located at an outer edge of the contact lens, or in close proximity to the outer edge. The microchannel is partially filled with an indicator solution that provides a visual indication of the microchannel change in volume, as the indicator solution is displaced along the microchannel in reaction to a volume change. Some embodiments may include a mesh, porous plug, valve, etc., in at least one of the one or more open end to keep the indicator solution from leaking out of the microchannel while allowing air to pass. For example, a one-way valve may use the fluid tension of the indicator solution and the small channel size to prevent back flow of the solution out of the microchannel. The flexible contact lens together with the microchannel design and the indicator solution allow for the device to capture fluctuating corneal curvature by correlating with fluctuation in the internal volume of the channel, according to movement of the indicator solution.

The indicator solution may be a liquid that is typically incompressible or substantially incompressible, to ensure maximum displacement within the microchannel in response to deformation of the contact lens. The indicator solution may be biocompatible and/or isotonic with the eye. Examples include oils (e.g., plant-based oils) and water-based solutions with naturally-occurring or added pigments, colour additives, or dyes. Examples of colour additives include, but are not limited to, those approved for use in medical devices and contact lenses according to the U.S. Code of Federal Regulations Title 21, Part 74, subpart D.

In various embodiments, the microchannel has a dimension and/or shape that is selected such that the change in volume in response to a selected amount of change in corneal curvature causes the indicator solution to be displaced sufficiently within the microchannel so that the displacement is detectable in an image captured by a digital camera. For example, the microchannel may have a substantial length so as to provide the required amount of change in volume. The substantial length may be achieved by providing the microchannel in a convoluted, zig-zag, coiled, spiral, and/or branched, etc., shape, and/or the microchannel may be configured to occupy a substantial portion of the surface area of the contact lens. In some embodiments, the microchannel occupies the outer region or periphery of the contact lens, so as to avoid, as much as possible, interfering with the vision of the person wearing the device. In some embodiments the microchannel may have a portion that is disposed along the entire periphery or most of the periphery of the contact lens, e.g., the microchannel may be disposed in 270-360° of the outer region of the lens. It will be appreciated from the below examples that the length of the microchannel may vary significantly, depending on the design. In various embodiments, the length of the microchannel may be, for example, about 140 mm to about 280 mm, although other lengths may be used. In some embodiments the microchannel is sufficiently long such that a reservoir for the indicator solution is not needed, resulting in more consistent and reliable response to changes in IOP. The microchannel may have a circular, rounded, rectangular, etc., cross-section, and an approximate diameter of about 60 µm to about 140 µm. In one embodiment the microchannel diameter is approximately 100 µm. In some embodiments there is a widening of the microchannel at the one or more open end. For example, the one or more open end may be widened to about 1 mm.

Non-limiting examples of such possible microchannel configurations are shown in FIGS. 1, 5A, 5B, and 5C. Of course, other configurations may be implemented to achieve substantially the same or similar results. Regardless of the configuration of the microchannel, at least one end of the microchannel is open, so that it is exposed to the atmosphere. Without wishing to be bound by theory, it is suggested that due to the micro-scale of the microchannel, a sealed microchannel experiences an internal vacuum/pressure build-up that may inhibit or halt the indicator solution movement. Providing the at least one end open to the atmosphere removes any such forces, and instead a pressure difference between the atmosphere and microchannel facilitates the indicator solution movement.

According to the embodiments, to detect a change in IOP of, e.g., 1 mmHg, the corresponding change in the microchannel volume is large enough to cause the indicator solution to be displaced sufficiently to be detected in a digital image taken by a readily-available camera. For example, the change in position of the indicator solution may be detected in images taken by a camera having a resolution typical of a smartphone camera or other electronic device, or other suitable camera, including, for example, a camera implemented in an eyeglasses frame or other mount that can be worn by the subject. The change in position of the indicator solution within the microchannel may be determined relative to one or more reference markers provided on the contact lens. The reference markers and the indicator solution are visible in the digital images.

Digital images of the contact lens are acquired and analyzed to detect locations of the indicator solution in the microchannel, and these are correlated to actual IOP. The images may be taken using a digital camera of a mobile device such as a smart phone, tablet, or laptop computer, etc., and therefore, the image may be easily taken by the subject without the need for specialized equipment and at any time of the day or night, without a professional's intervention.

An application running on the mobile device used to obtain the digital images, or on a remote device, may include an algorithm that provides image analysis required to determine IOP from the images, and may provide substantially instant feedback about the subject's IOP. For example, a software application as described in U.S. Patent Application Publication No. 2017-0280997-A1 may be used. The application may prompt the subject to obtain images at selected times or according to a selected schedule. In the case of a camera worn by the subject, such as a camera implemented in an eyeglasses frame, the camera may communicate with the device running the software application (e.g., via Bluetooth®), and the application may direct the camera to acquire images automatically, e.g., at selected times or according to a selected schedule. This may include notifying the subject when an image is being acquired, so that the subject's eye is open for proper image acquisition. The application may conduct a preliminary analysis of an acquired image to ensure its suitability (i.e., sufficient quality) for determining IOP, and reject unsuitable images and acquire further images until a suitable image is obtained. The images may be stored on the device, and accumulated for later uploading to a server (e.g., at a doctor's office) at a selected or prescribed time or schedule using a wired or wireless connection. Alternatively, the images may be uploaded substantially immediately as acquired if a suitable connection is available.

Embodiments may be constructed using a flexible polymer material suitable for contact lens applications. The material should be chosen so that a contact lens is hydrophilic for proper interaction with the tear film. A contact lens prepared from a hydrophobic material may be subjected to suitable surface treatment to achieve hydrophilicity. For extended wear the contact lens may be oxygen-permeable, e.g., about 6 to about 150 Dk/t.

The material may comprise silicone (e.g., polydimethyl siloxane (PDMS)). Other materials such as polymethyl methacrylate (PMMA) may be used in some embodiments, although such material is less flexible. The material may comprise a hydroxyethylmethacrylate (HEMA), which may be in the form of a hydrogel such as a polyHEMA, or a HEMA cross-linked with ethylene dimethacrylate (EDMA) or ethylene glycol dimethacrylate (EGDMA). In some embodiments combinations of two or more such materials may be used, such as a silicone-hydrogel, a HEMA hydrogel, or a HEMA/MAA. Silicone hydrogel contact lenses have a high oxygen permeability, typically >100 Dk. In some embodiments a readily available (i.e., off-the-shelf) lens may be used, which may be machined or modified to obtain the desired microchannel. Embodiments may be constructed by one or more of: molding a lens including a microchannel; machining a microchannel into a lens; and applying a microchannel to a lens. Molding may include preparing a 3D mold with the microchannel features using a high speed micromilling machine.

For example, a silicone polymer is hydrophobic, despite its high oxygen permeability. Therefore, silicone is not ideal as a homopolymer contact lens material. However, a copolymer of silicone with a hydrophilic (highly polar) monomer can solve this problem. Copolymerization may also be used to enhance physical properties through the cross-linking of polymer chains by adding molecular weight to the chain. In some cases, adding a soft polymer can reduce the modulus of a particularly rigid material (often a silicone-based material). Hydrophobic co-monomers add oxygen permeability to materials that require improvement in this property, and silicone-based monomers are often used for this purpose.

The invention is further described by way of the following non-limiting Examples.

EXAMPLE 1

Figure 1:
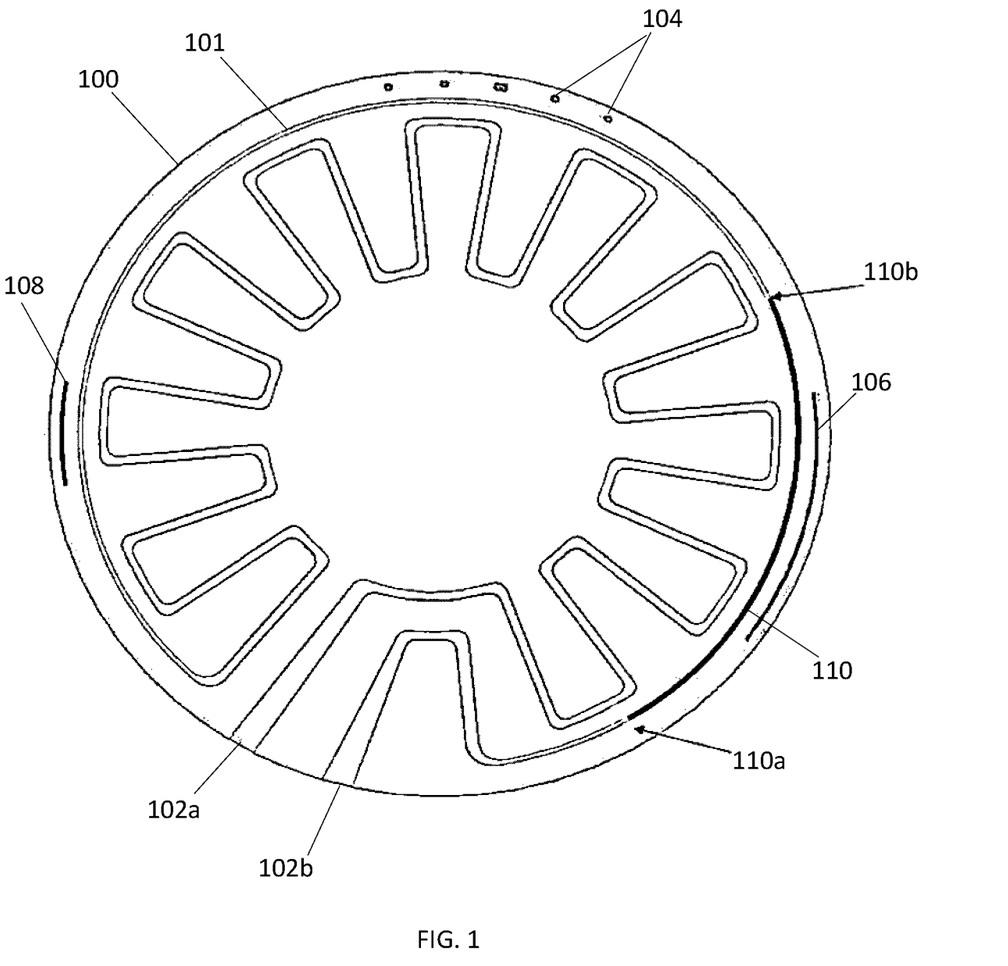
FIG. 1 is a diagram of an IOP measuring device according to one embodiment.
Figure 2:
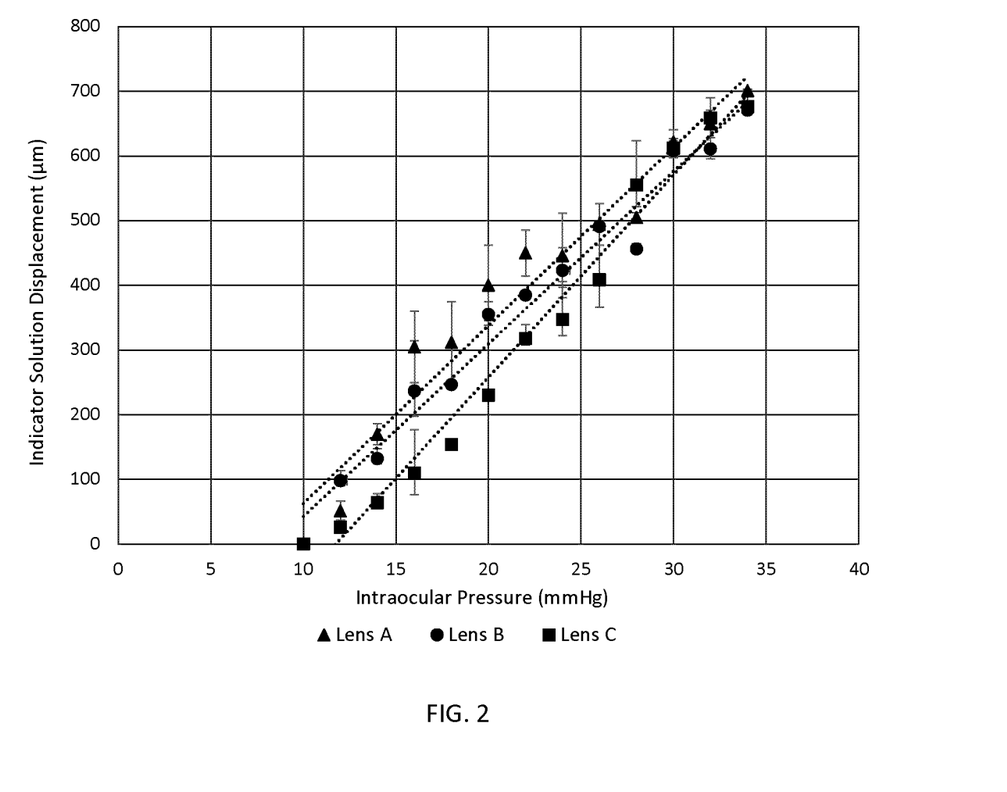
FIG. 2 is a plot showing indicator solution displacement as a function of intraocular pressure for three devices (A, B, C) based on the embodiment of FIG. 1 in an experiment using porcine eyes; each data point is the average of two measurements, error bars show standard deviation.

An embodiment of the device is shown diagrammatically in FIG. 1. As shown in FIG. 1, a flexible contact lens 100 approximately 250 µm thick was made from polydimethylsiloxane (PDMS). The contact lens was manufactured with an embedded microchannel 101 with a cross section of approximately 100 µm×100 µm, with a cover layer (not shown) that covered the base and sealed the microchannel. The microchannel had an inlet 102a and an outlet 102b which were tapered to about 1 mm at the openings to allow for injecting the indicator solution, shown darkened at 110, into the microchannel. The microchannel had two sections, an inner "zig-zag" or "crenellated" section with an approximate diameter of 100 µm and an outer section without sharp curves or changes in direction (e.g., substantially linear, or curvature with constant or varying radius such as a smooth arc or other shape), and approximate diameter of 80 µm close to the outer edge of the lens. The total length of the microchannel was about 260 mm. In this embodiment the indicator solution was disposed in the outer section of the microchannel but not in the inner zig-zag section. This avoids any impediment to movement of the indicator solution in the microchannel that may be presented by sharp bends and changes in direction in the microchannel. Various reference markers 104, 106, 108 were embedded into the contact lens. In this embodiment it can be seen how the position of the indicator solution 110 in the microchannel 101 can be determined according endpoints 110a and 110b of the indicator solution relative to the reference marker 106. It will be appreciated that other shapes, patterns, etc., of the inner section of the microchannel, other than a zig-zag pattern, may be used in order to achieve a selected total length of the microchannel (e.g., about 140 mm to about 300 mm) that provides detectable movement of the indicator solution in response to a change in IOP.

The contact lens was manufactured using a casting process. Mold components were manufactured from aluminum using a Model 363-S micro-milling machine (Microlution, Inc.), with a feed rate of 8,000 rpm. PDMS was used as the main material for the contact lens device for its flexibility and oxygen permeability, and is a known FDA approved biocompatible material, already used to manufacture soft contact lenses. Elasticity of the PDMS can be modified based on the amounts (i.e., ratio) of pre-polymer and curing agent used. For example, whereas a ratio of 10:1 is common, the ratio was optimized herein to have as low an elastic modulus as possible without the presence of the adhesive properties that can occur. For this embodiment, the ratio was optimized at 15:1. First, PDMS pre-polymer and curing agent were mixed at a ratio of 15:1 and poured into the mold. The mold was placed in a vacuum chamber for 40 minutes for degassing, until substantially all air bubbles disappeared. The mold was placed in an oven at 65° C. for 40 minutes and then was cooled to room temperature, and then the contact lens was released from the mold. A thin, approximately 100 µm, cover layer was made using a similar casting process, with a smooth mold. The two components (base and cover layer) were surface treated using a Corona Treater (Electro-Technic Products Inc., Chicago, IL, USA), then bonded together for a total lens thickness of 250 µm. For the indicator solution, dyed biocompatible avocado oil was injected into one of the open ends of the microchannel. One of the ends of the microchannel was then sealed with PDMS while the other end was left open to the atmosphere. Avocado oil was selected as the indicator solution due to its heavy molecule structure, making it unable to evaporate from the PDMS while having sufficient colour to visually track its movement throughout the microchannel. The indicator solution was positioned far enough away from the open end to avoid the possibility of it leaking out of the microchannel.

EXAMPLE 2

Performance of an embodiment as shown in FIG. 1 and as described in Example 1 was evaluated in a series of experiments using fresh enucleated porcine eyes. Porcine eyes were chosen for their similarities in shape and mechanical properties to human eyes. Testing was performed with a slow and constant stress applied to an eye while a contact lens directly measuring the strain. To mitigate any unwanted affects from the eye drying out and to add a tear layer to the system, water was dripped onto the porcine eye throughout the experiments.

For the tests, a porcine eye was placed on an eye holder with a loose fit to allow for unrestricted expansion/contraction of the eye, to avoid any unwanted affect on the IOP. Tubing connected to a syringe pump was inserted into the sclera of the eye. The syringe pump, filled with water, was used to manually simulate changes in IOP at a controlled rate between 10 to 34 mmHg. Real time IOP was monitored with a Miller Micro-Tip Pressure Catheter Transducer threaded into an opposite side of the sclera. The contact lens was placed onto the centre of the cornea and cameras (Duratool Model S02 USB Digital Microscope) recorded the top view and side view of the eye throughout the experiment. The side view of the eye was used to ensure the contact lens had proper connection and placement and to confirm that deformation of the eye curvature did occur, while the top view recorded the indicator solution movement.

Figure 3:
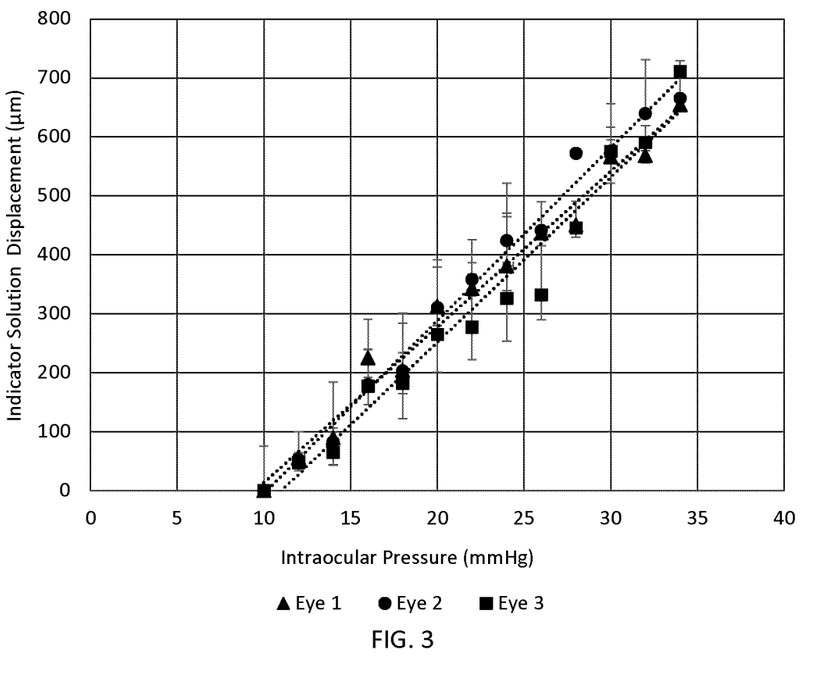
FIG. 3 is a plot showing indicator solution displacement as a function of intraocular pressure for one device based on the embodiment of FIG. 1 in an experiment using three porcine eyes; each data point is the average of two measurements, error bars show standard deviation.

To evaluate reliability, responsiveness, and inter-device agreement, three contact lens devices were each tested two times on a single eye. At baseline and at every 2 mmHg step increase in IOP from 10 mmHg to 34 mmHg, an image of the contact lens device was captured. Absolute displacement of the indicator solution was calculated by comparing to a reference marker (e.g., such as 104, 106, 108 in FIG. 1). For all three devices and trials, the indicator solution showed a similar linear relationship between solution displacement and IOP (FIG. 3). The average indicator solution displacement between the trials was 28.5 µm/mmHg with a standard deviation of 2.4. The small differences between devices in indicator solution movement may have resulted from inconsistencies introduced in fabrication, the effects of positioning of the lens on the eye or small errors introduced by the micro-catheter pressure transducer used to determine the a standard IOP measure.

To evaluate the ability of the embodiment to reliably detect the IOP of different eyes, a single device was tested on three eyes. The three tested eyes had different corneal size, shape and thickness, with related differences in biomechanical properties, which represent typical variations from eye to eye. Similar to the above experiment, the indicator solution was analysed at baseline and at every 2 mmHg increase in IOP from 10 mmHg to 34 mmHg. For all three eyes the indicator solution movement showed a similar linear relationship with increasing IOP at slopes of 26.4, 29.3, and 28 µm/mmHg for eye 1, 2 and 3, respectively (FIG. 3), resulting in an average indicator solution movement between trials of 27.9 µm/mmHg with a standard deviation of 1.5. The consistent results demonstrate the robustness of the IOP device to physiological variations, i.e., the device provides reliable TOP measurement for different eyes. Based on the experimental results, it may be concluded that the flexibility of the contact lens device allows it to overcome variations in physiology between porcine eyes. It is expected that similar performance would be obtained for human eyes.

Figure 4A:
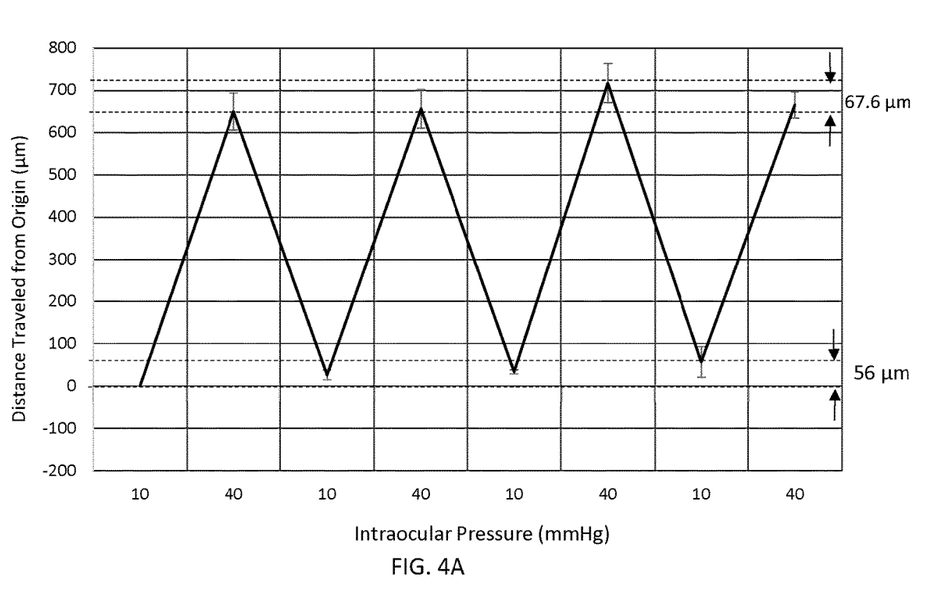
FIGS. 4A and 4B are plots showing indicator solution displacement as a function of fluctuating intraocular pressure for one device based on the embodiment of FIG. 1 in an experiment using a porcine eye.
Figure 4B:
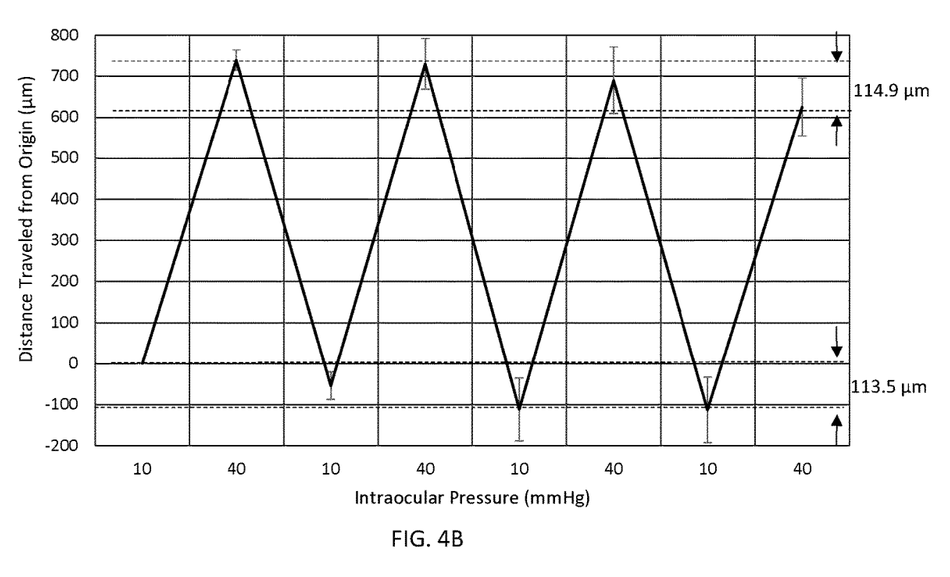

To accurately track fluctuations in IOP over an extended period, such as a day, the device must allow indicator solution travel in an anterograde direction with increases in TOP and a retrograde direction with decreases in IOP, over multiple cycles, with high repeatability. Therefore, to evaluate this capability, IOP was cycled between 10 mmHg and 40 mmHg for a total of four cycles and the indicator solution position was determined from camera images. There were noticeable differences in results depending on the tracking point of the indicator solution used. The outer tracking point (110a in FIG. 1) yielded more consistent results compared to the inner tracking point (110b in FIG. 1); see FIGS. 4A and 4B, respectively. For the outer tracking point there was a maximum variance in the indicator solution position of 56.7 µm when the pressure was 10 mmHg and 67.6 µm when the pressure was 40 mmHg. The indicator solution returned 92% of the way back to the original position for the outer tracking point and 85% for the inner tracking point. It is believed that the difference is due to microchannel retention of the indicator solution; for example, retention of the indicator solution on the sidewalls of the microchannel reduces the effective volume of the indicator solution. As fluid retention within the microchannel increases—with multiple trials—the decrease in the initial volume of the indicator solution has a differential effect on the tracking points.

EXAMPLE 3

Figure 5A:
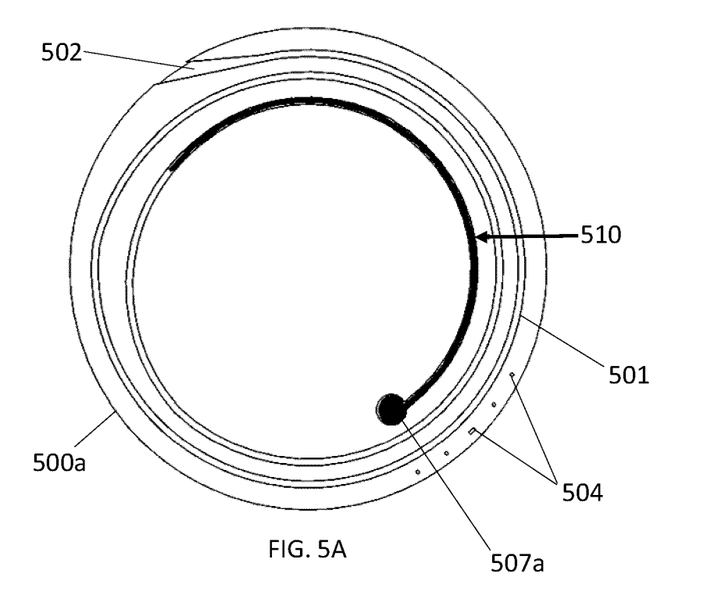
FIGS. 5A, 5B, and 5C are diagrams of IOP measuring devices according to further embodiments.
Figure 5B:
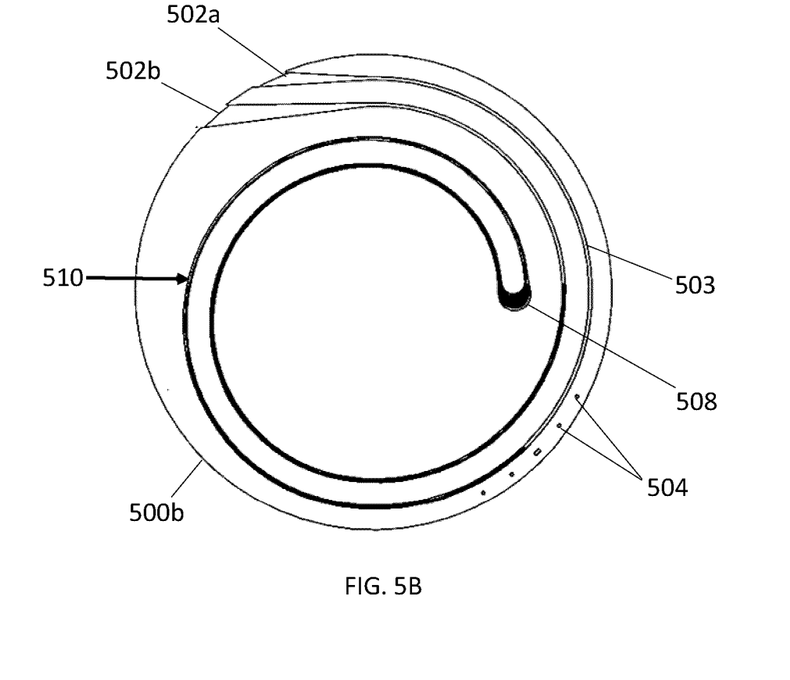

Alternative embodiments are shown in FIGS. 5A and 5B. In the embodiment of FIG. 5A the contact lens device 500a has a microchannel 501 in a single spiral configuration with an approximate diameter of 100 µm and total length of about 180 mm, and an open end 502 that was tapered to about 1 mm. Reference markers 504 are provided along an edge of the device. An indicator solution, shown darkened at 510, is disposed in a portion of the microchannel. Optionally, a reservoir 507a for the indicator solution may be disposed at the end of the microchannel 501.

The embodiment of FIG. 5B is similar to that shown in FIG. 5A, except that the microchannel 503 is in a double spiral configuration, such that both ends 502a, 502b are open to the atmosphere. The microchannel has an approximate diameter of 100 µm and total length of about 190 mm, and open ends 502 that are tapered to about 1 mm. An indicator solution 510 is disposed in a portion of the microchannel. Optionally, a widening of the microchannel may be provided at a point 508 where the two microchannel spirals are connected.

The embodiments of FIGS. 5A and 5B were manufactured in PDMS pre-polymer and curing agent at a ratio of 15:1 using micro-machined aluminum molds in the same manner as described in Example 1.

Figure 6A:
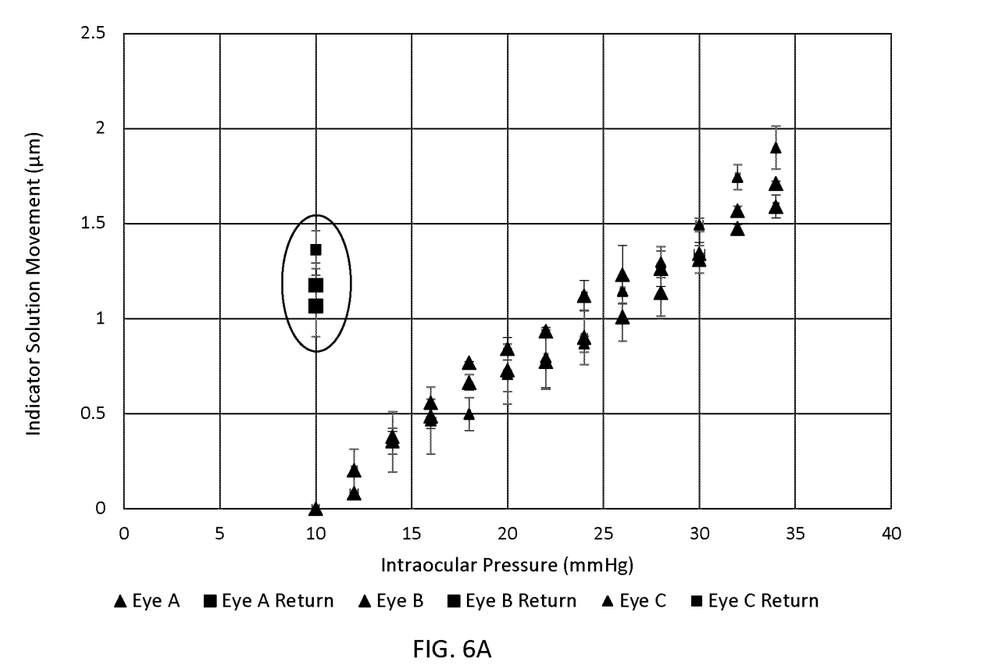
FIGS. 6A and 6B are plots showing indicator solution displacement as a function of intraocular pressure for the embodiments of FIGS. 5A and 5B, respectively, in experiments using porcine eyes, wherein each data point is the average of two measurements and error bars show standard deviation.
Figure 6B:
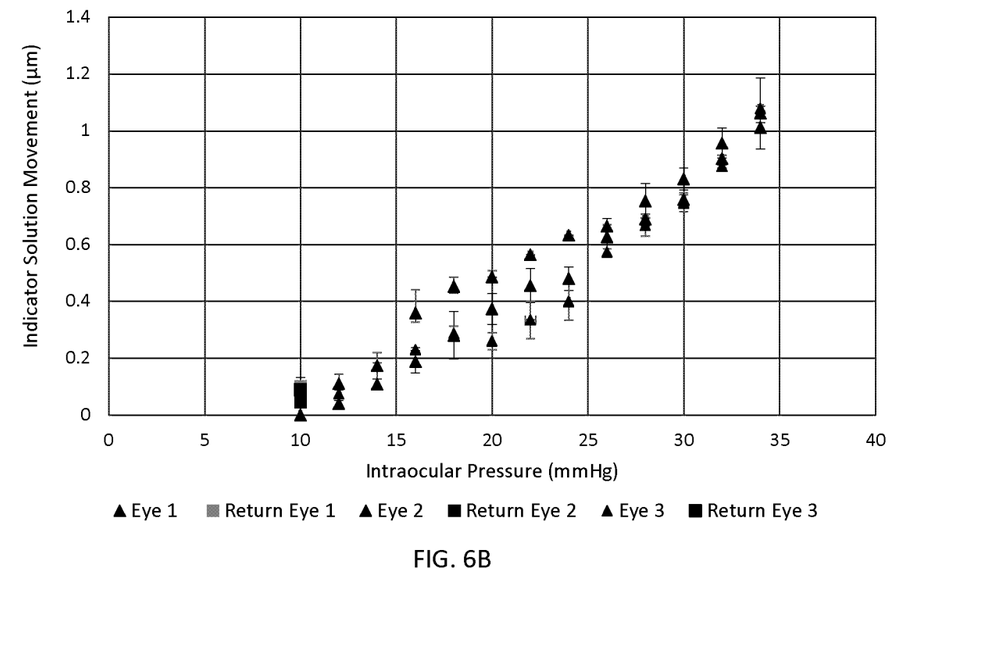

FIGS. 6A and 6B show results of preliminary tests of the embodiments of FIGS. 5A and 5B, respectively. The methods were as described in Example 2. One device of each embodiment was fitted to three different porcine eyes, and two trials were completed for each eye. For each trial, images of the device were obtained for 2 mmHg increments in IOP from 10 mmHg to 34 mmHg, and then back to 10 mmHg. The error bars in the plots of FIGS. 6A and 6B show the standard deviation for the two trials that were conducted from a single contact lens, on a single eye at each IOP increment.

From FIGS. 6A and 6B it can be seen that the single spiral embodiment of FIG. 5A was more sensitive, i.e., there was greater movement of the indicator solution per increment in IOP. From the average slopes the performance was determined to be about 72 µm/mmHg for the single-spiral embodiment, and about 44 µm/mmHg for the double-spiral embodiment. However, in the single-spiral embodiment the indicator solution did not return to the starting position when the IOP was lowered back to 10 mmHg (see the points circled in FIG. 6A). As a result, the overall return rate of this embodiment was 30.7%. In contrast, in the double-spiral embodiment the indicator solution did return to the starting position when the IOP was lowered back to 10 mmHg. As a result, the overall return rate of this embodiment was 98%.

Figure 5C:
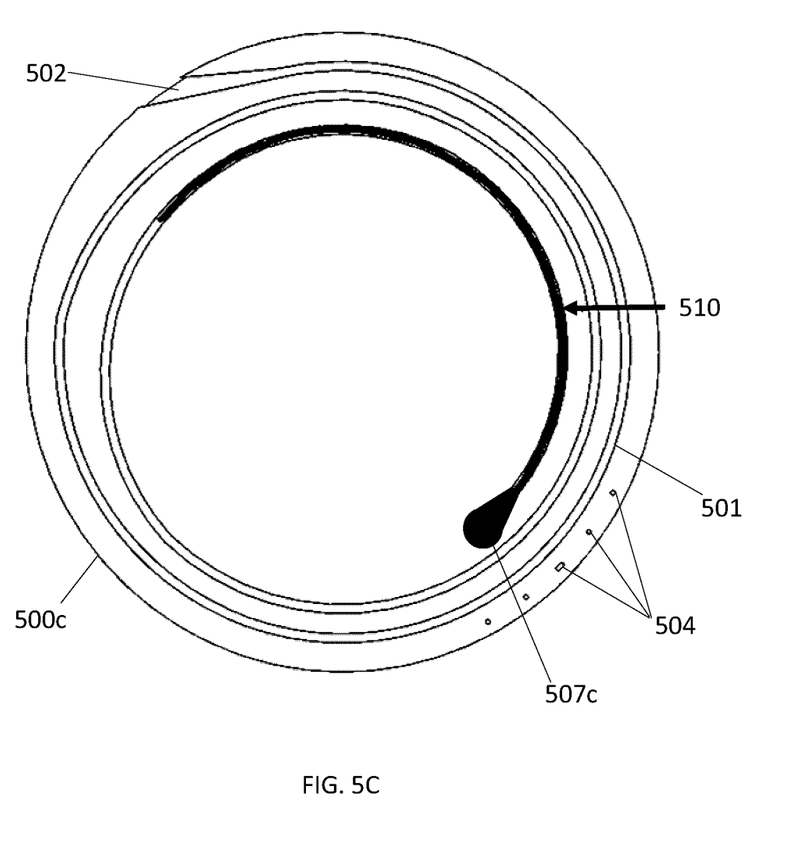

A further embodiment is shown in FIG. 5C. In this embodiment, which is similar to FIG. 5A, the contact lens device 500c has a microchannel 501 in a single spiral configuration with an approximate diameter of 100 µm and total length of about 180 mm, and with an open end 502 that was tapered to about 1 mm. Reference markers 504 are provided along an edge of the device. An indicator solution 510 is disposed in a portion of the microchannel. In this embodiment, a reservoir 507c for the indicator solution is disposed at the end of the microchannel 501. Unlike the optional reservoir 507a of FIG. 5A, in this embodiment there is a smooth curved or linear transition (i.e., without corners or angles) from the reservoir 507c to the microchannel 501 to facilitate movement of the indicator solution.

EXAMPLE 4

Figure 7A:
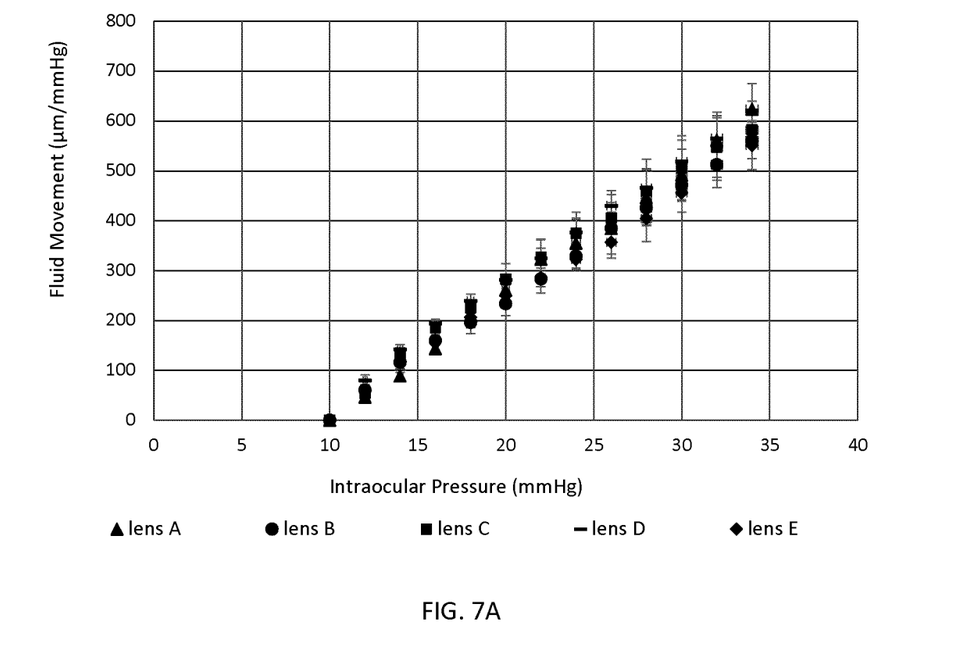
FIGS. 7A and 7B are plots showing the effect of central corneal thickness and radius of corneal curvature on the indicator solution displacement as a function of intraocular pressure for the embodiment of FIG. 1, in experiments using porcine eyes.
Figure 7B:
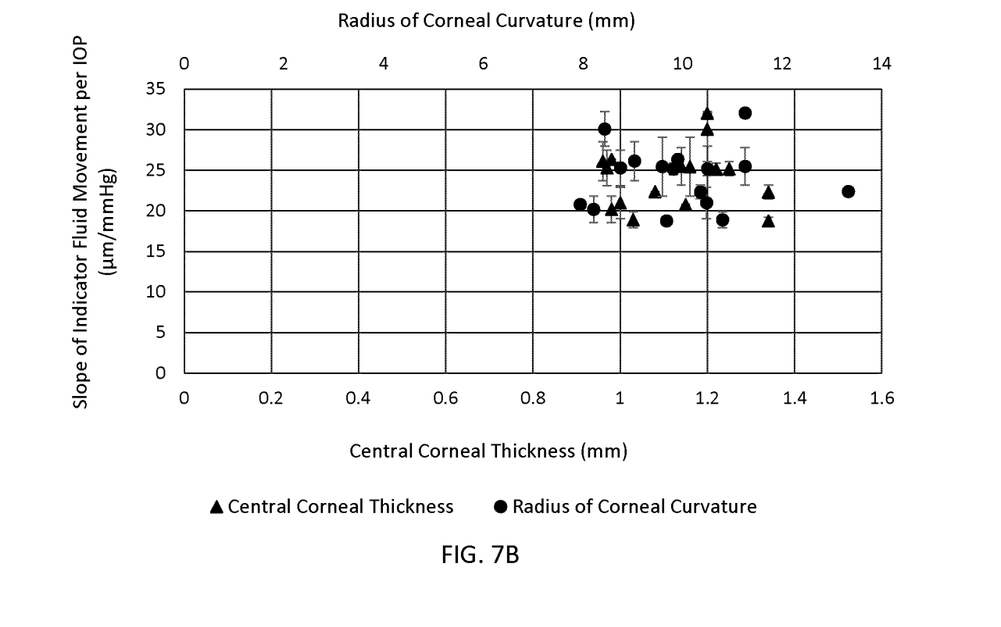

To evaluate the effect of the physiological variations in the central corneal thickness and the radius of corneal curvature on the association between indicator solution to displacement and intraocular pressure, five devices (based on the embodiment of FIG. 1) were tested on 16 porcine eyes, with one to three devices tested on each eye and two trials completed per device. The central corneal thickness and radius of corneal curvature were measured using ultrasound bio-microscopy (UBM). Similar to the above experiments, the indicator solution position was analysed at baseline and after every 2 mmHg increase in TOP from 10 mmHg to 34 mmHg. FIG. 7A shows that all five devices performed similarly, with strong linear slopes of 25.54, 22.86, 24.04, 24.61, and 22.08 µm/mmHg. To further examine the impact of physiological variations, the slopes of the indicator solution movement as a function of the IOP were plotted against the measured central corneal thickness and radius of corneal curvature for the 16 eyes. FIG. 7B shows that there was no correlation between the physiological variations measured and the movement of the indicator solution as a result of the IOP fluctuations.

All cited documents are incorporated herein by reference in their entirety.

Equivalents

Those of ordinary skill in the art will recognize, or be able to ascertain through routine experimentation, equivalents to the embodiments described herein. Such equivalents are within the scope of the invention and are covered by the appended claims.

The invention claimed is:

1. A device for monitoring intraocular pressure (IOP) of an eye of a subject, comprising:
    a flexible lens that is adapted to fit on the eye and to change curvature in response to a change in curvature of the eye;
    a microchannel disposed in or on the lens, the microchannel having one or more ends, wherein at least one end is open to a surrounding environment of the lens;
    an indicator solution disposed in a portion of the microchannel;
    wherein the microchannel exhibits a change in volume in response to a change in curvature of the lens;
    wherein the change in volume of the microchannel results in a change in position of the indicator solution in the microchannel;

wherein the change in position of the indicator solution in the microchannel is indicative of a change in IOP.

2. The device of claim 1, wherein the microchannel has a first end and a second end, wherein the first end and the second end are open to the surrounding environment of the lens.

3. The device of claim 1, comprising:
at least one reference marker disposed on the lens;
wherein the change in position of the indicator solution in the microchannel is determined relative to the at least one reference marker.

4. The device of claim 3, wherein the at least one reference marker and the indicator solution are visible in digital images of the device.

5. The device of claim 1, comprising a mesh, a porous plug, or a valve disposed in the at least one open end of the microchannel.

6. The device of claim 1, wherein the microchannel comprises a first section configured linearly or in a smooth arc and a second section configured in a convoluted, zig-zag, coiled, spiral, and/or branched shape along a substantial portion of its length.

7. The device of claim 6, wherein the indicator solution is disposed in the first section of the microchannel.

8. The device of claim 1, wherein the microchannel is configured to occupy an outer region of the lens.

9. The device of claim 1, wherein the indicator solution comprises oil or a water-based solution with a naturally-occurring or added pigment, colour additive, or dye.

10. A system for measuring and/or monitoring intraocular pressure (IOP) of an eye of a subject, comprising:
the device of claim 1; and
at least one camera;
wherein the at least one camera is adapted to be worn by the subject and to acquire digital images of the device fitted to the eye of the subject.

11. The system of claim 10, wherein the at least one camera is implemented in a frame that is adapted to be worn by the subject.

12. The system of claim 11, wherein the frame is an eyeglasses frame.

13. The system of claim 10, further comprising a software application that is adapted to control acquiring of digital images by the at least one camera.

14. A method for measuring and/or monitoring intraocular pressure (IOP) of an eye of a subject, comprising:
fitting a flexible lens on the eye, the flexible lens being adapted to change curvature in response to a change in curvature of the eye;
wherein the flexible lens comprises a microchannel, the microchannel having at least one end that is open to a surrounding environment of the lens, wherein the microchannel exhibits a change in volume in response to a change in curvature of the lens, and an indicator solution disposed in a portion of the microchannel;
detecting a change in position of the indicator solution in the microchannel; and
correlating the change in position of the indicator solution with a change in IOP.

15. The method of claim 14, wherein the microchannel has a first end and a second end, wherein the first end and the second end are open to the surrounding environment of the lens.

16. The method of claim 14, wherein the microchannel comprises a first section configured linearly or in a smooth arc and a second section configured in a convoluted, zig-zag, coiled, spiral, and/or branched shape along a substantial portion of its length.

17. The method of claim 16, wherein the indicator solution is disposed in the first section of the microchannel.

18. The method of claim 14, wherein the microchannel is configured to occupy an outer region of the lens.

19. The method of claim 14, comprising capturing two or more digital images of the lens at two or more instants in time, respectively; and
detecting the change in position of the indicator solution in the microchannel as a difference between the two or more digital images.

20. The method of claim 19, wherein the digital images are captured using a digital camera of a personal computing device.

21. The method of claim 20, wherein the personal computing device is a smartphone.

22. The method of claim 19, wherein the digital images are captured using a digital camera adapted to be worn by the subject.

23. The method of claim 14, wherein the flexible lens further comprises at least one reference marker;
wherein the change in position of the indicator solution in the microchannel is determined relative to the reference marker.

* * * * *